US00PP13910P39

(12) United States Plant Patent
Noodelijk

(10) Patent No.: US PP13,910 P3
(45) Date of Patent: Jun. 24, 2003

(54) CHRYSANTHEMUM NAMED 'YELLOW REAGAN MUNDO'

(75) Inventor: Robert Noodelijk, Woubrugge (NL)

(73) Assignee: Chrysanthemum Breeders Association (NL)

( * ) Notice: Subject to any disclaimer, the term of this patent is extended or adjusted under 35 U.S.C. 154(b) by 0 days.

(21) Appl. No.: 09/906,690

(22) Filed: Jul. 18, 2001

(65) Prior Publication Data

US 2003/0024024 P1 Jan. 30, 2003

(51) Int. Cl.[7] ..... A01H 5/00
(52) U.S. Cl. ..... Plt./295
(58) Field of Search ..... Plt./295

(56) References Cited

U.S. PATENT DOCUMENTS

PP7,682 P * 10/1991 Shoesmith et al. ..... Plt./74

OTHER PUBLICATIONS

UPOV–ROM hits on 'Yellow Reagan Mundo', GTI Jouve Retrieval Software, Plant Variety Database, 2001/06.*

* cited by examiner

*Primary Examiner*—Bruce R. Campell
*Assistant Examiner*—Anne Marie Grünberg
(74) *Attorney, Agent, or Firm*—Parkhurst & Wendel, L.L.P.

(57) ABSTRACT

A Chrysanthemum plant named 'Yellow Reagan Mundo' characterized by its medium sized blooms with yellow ray-florets and yellow-green disc florets.

1 Drawing Sheet

RELATED APPLICATIONS

'Yellow Reagan Mundo' is related to 'Pearl Reagan Mundo' (unpatented) and 'Dark Reagan Mundo' (copending application Ser. No. 09/906,688). 'Yellow Reagan Mundo' is a natural sport of 'Pearl Reagan Mundo'.

BACKGROUND OF THE INVENTION

'Yellow Reagan Mundo' is a product of a breeding and selection program which had the objective of finding color mutants of 'Pearl Reagan Mundo'. The new plant of the present invention comprises a new and distinct cultivar of chrysanthemum plant that is a natural occuring sport of a parent chrysanthemum named 'Pearl Reagan Mundo'. A comparison with parent chrysanthemum 'Pearl Reagan Mundo' is also made in this application. The new cultivar was discovered as a whole plant mutation in September 1996 by Rob Noodelijk in a controlled environment (greenhouse) in Rijsenhout, Holland. The first act of asexual reproduction of 'Yellow Reagan Mundo' was accomplished when vegetative cuttings were taken from the initial selection in November 1996 in Rijsenhout, Holland.

SUMMARY OF THE INVENTION

The present invention is a new and distinct variety of chrysanthemum bearing medium sized blooms with yellow ray-florets and yellow-green disc florets.

BRIEF DESCRIPTION OF THE DRAWINGS

The present invention of a new and distinct variety of chrysanthemum is shown in the accompanying drawing, the color being as nearly true as possible with color photographs of this type.

FIG. 1 shows a stem of the cultivar in full bloom.

DESCRIPTION OF THE INVENTION

This new variety of chrysanthemum is of the botanical classification *Chrysanthemum morifolium.* The observations and measurements were gathered from plants grown in April / May in a greenhouse in Rijsenhout, Holland in a photo-periodic controlled crop under conditions generally used in commercial practice. The greenhouse temperatures during this crop were at day-time between 18° C. and 25° C. and at night 20° C. After a long day period of 14 days, the photo-periodic response time in this crop was 50 days. After the long day period to flowering, growth retardents were applied 2 to 3 times in an average dose of 2.5 gram / liter water. No tests were done on disease or insect resistance or susceptibility. This new variety produces medium sized blooms with yellow ray-florets and yellow-green disc-florets blooming on the plant for 28 days. This new variety of chrysanthemum has been found to retain its distinctive characteristics throughout successive propagations. However, the phenotype may vary significantly with variations in environment such as light intensity and temperature. To show the phenotype as described, 'Yellow Reagan Mundo' may be planted without assimilation lightning between week 50 and 40 under greenhouse conditions in Holland. With assimilation lightning (minimum level 2500 lux), it may be planted year round under greenhouse conditions in Holland.

From the cultivars known to inventor the most similar existing cultivars in comparison to 'Yellow Reagan Mundo' are 'Pearl Reagan Mundo' 'Yellow Reagan', and 'Sunny Elite Reagan'.

When 'Yellow Reagan Mundo', 'Pearl Reagan Mundo', 'Yellow Reagan' and 'Sunny Elite Reagan' are being compared, the following differences and similarities are noticed.

(A) The difference of 'Yellow Reagan Mundo' and 'Pearl Reagan Mundo' is the flower color for which characteristic 'Yellow Reagan Mundo' has been selected out of 'Pearl Reagan Mundo'. All other characteristics of 'Yellow Reagan Mundo' and 'Pearl Reagan Mundo' are the same.

(B) The differences of 'Yellow Reagan Mundo' and 'Yellow Reagan' are (1) flower size, (2) spray formation and flower count, and (3) tolerance for a lower night temperature. All other characteristics of 'Pearl Reagan Mundo' and 'Reagan' are similar.

(C) The differences of 'Yellow Reagan Mundo' and 'Sunny Elite Reagan' are (1) size and color of the flower disc, (2) growth rate, (3) spray formation, and (4) tolerance for a lower night temperature. All other characteristics of 'Yellow Reagan Mundo' and 'Sunny Elite Reagan' are similar.

(A) Flower color: 'Yellow Reagan Mundo' has yellow ray-florets instead of purple ray-florets.

(B) (1) Flower size: The flower of 'Yellow Reagan Mundo' is a little smaller. (2) The spray formation: The spray formation of 'Yellow Reagan Mundo' is more flat, less pyramidal, a little wider and the flower count is higher. (3) Temperature tolerance: 'Pearl Reagan Mundo' and all its color mutants can be grown at a lower night temperature. The required minimum night temperature to grow successfully a flowering crop of 'Yellow Reagan' is 17° C. Grown under night temperatures lower than 17° C. 'Reagan' will not come into flower. Under high light conditions, 'Pearl Reagan Mundo' can be successfully grown at a night temperature as low as 14° C. This has been tested and confirmed in poor heated crops under high light conditions flowering in February 1997 and 1998 in Italy and Spain.

(C) (1) The flower disc of 'Yellow Reagan Mundo' is not so small and not so green as the flower of 'Sunny Elite Reagan'. (2) The growth of 'Yellow Reagan Mundo' is less vigorous. (3) The spray formation of 'Yellow Reagan Mundo' is more spreading, showing a bigger angle of the peduncles with the stem. The spray-formation of 'Sunny Elite Reagan' is more upright showing a smaller angle of the peduncles with the stem. (4) The most essential difference: 'Sunny Elite Reagan' does not have the lower night temperature tolerance as 'Yellow Reagan Mundo'. 'Sunny Elite Reagan' must be grown at a night temperature of at least 17° C. 'Yellow Reagan Mundo' can be grown at a night temperature as low as 14° C.

The following is a description of the plant and characteristics that distinguish 'Yellow Reagan Mundo' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, 1995 edition.

Botanical Description of Cultivar 'Yellow Reagan Mundo'

Bud:

*Size.*—Medium Cross-section 1.0 cm , height 0.7 cm.

*Outside color.*—Yellow 10 C.

*Involucral bracts.*—2 rows, length 7 mm, width 3 mm.

*Involucral bracts among disc-florets.*—Not present.

*Involucral bracts color.*—Green 138 B.

Bloom:

*Type.*—Single.

*Height.*—Flat, 1.5 cm.

*Size.*—Medium.

*Fully expanded.*—6–6.5 cm.

*Number of blooms per single stem.*—Average of 12–14.

*Seeds.*—Produced in small quantities, ovate shaped. Grey-brown 199 A, 1.5 mm in length.

*Performance* (*blooming period*).—28 days.

Color:

*Center of the flower* (*disc-florets*).—Immature Yellow-green 144 A in the center to yellow 12 A along the border, mature Yellow 12 A with a dot of yellow-green 144 A in the center.

*Color of upper surface of the majority of the ray-florets.*—Yellow 10 A.

*Color of the lower surface of the majority of the ray-florets.*—Yellow 10 C.

*Tonality from distance.*—A yellow daisy with a yellow-green disc.

*Discoloration to color.*—To Yellow 10 C.

Ray florets:

*Texture.*—Upper and under side smooth.

*Number.*—26–30 (two rows).

*Cross-section.*—Convex.

*Longitudinal axis of majority.*—Slightly reflexing sometimes twisted.

*Length of corolla tube.*—Very short.

*Ray-floret length.*—3.5 cm.

*Ray-floret width.*—1.2 cm.

*Ratio length / width.*—Medium.

*Shape of tip.*—Pointed, sometimes dentate.

Disc florets:

*Disc diameter* (*when visible*).—Medium (1.5 cm).

*Distribution of disc florets.*—Numerous, visible at all stages of flowering.

*Type.*—Tubular.

*Color.*—Immature Yellow-green 144 A, mature yellow 12 A.

*Receptacle shape.*—Conical raised.

Reproductive organs:

*Stamen* (*present in disc florets only*).—Yellow, thick, 3 mm in length.

*Stamen color.*—Yellow 12 B.

*Pollen.*—Present.

*Pollen color.*—Yellow-orange 15 A.

*Styles* (*present in both ray and disc florets*).—Green, thick.

*Style color.*—Green 143 B.

*Style length.*—5 mm.

*Stigmas.*—Green 143 B.

*Stigma width.*—1 mm.

*Ovaries.*—Enclosed in calyx.

Plant:

*Form.*—A spray mum meant for erect culture.

*Growth habit.*—Erect.

*Growth rate.*—Medium.

*Height.*—100–110 cm.

*Internodes.*—2.5–3.0 cm.

*Spray formation.*—Corymbiform (funnel-shaped with a flat umbel on top).

*Peduncle length.*—Near the top 14 cm, near the middle 21 cm, near the bottom 26 cm.
*Peduncle color.*—Green 138 B.
*Peduncle, attachment.*—Good, not brittle.
*Peduncle, angle with stem.*—Small, 40°.
*Stem color.*—Yellow-green 138 B.
*Stem strength.*—Medium to strong.
*Stem brittleness.*—Absent.
*Stem anthocyanin coloration.*—Present, a thin layer of greyed-red 180 D at the base of the stem.
*Flowering response* (*photo-periodic controlled crop, not natural season*).—50 days.

Foliage:
*Color.*—Upper side green 137 A, Under side green 137 C.
*Size.*—Length 12 cm, width 9 cm.
*Petiole length.*—2.0 cm.
*Petiole color.*—Yellow- green 138 B.
*Quantity* (*number per single stem*).—26–32.
*Shape.*—Oval.
*Texture upper side.*—Scabrous.
*Texture under side.*—Pubescent.
*Venation arrangement.*—Palmate.
*Shape of the margin.*—Lobed.
*Shape of base of sinus between lateral lobes.*—Round.
*Margin of sinus between lateral lobes.*—Converging sometimes asymmetric.
*Shape of base.*—Rounded.
*Apex.*—Mucronate.

Differences with comparison varieties

| | 'Yellow Reagan Mundo' | 'Pearl Reagan Mundo' | 'Yellow Reagan' | 'Sunny Elite Reagan' |
|---|---|---|---|---|
| Color of Ray florets | Yellow 10 A | Purple 75 D | Yellow 5 C | Yellow 5 A |
| Flower disc size | 1.5 cm | 1.3–1.5 cm | 1.5 cm | 1.0–1.2 cm |
| Growth rate | Medium | Medium | Medium | Vigorous |
| Height | 100–110 cm | 100–115 cm | 100–125 cm | 105–130 cm |
| Peduncle, angle with stem | 40° | 40° | 30°–35° | 30° |
| Required minimum night temperature | 14° C. | 14° C. | 17° C. | 17° C. |

I claim:
1. A new and distinct variety of chrysanthemum plant as described and illustrated.

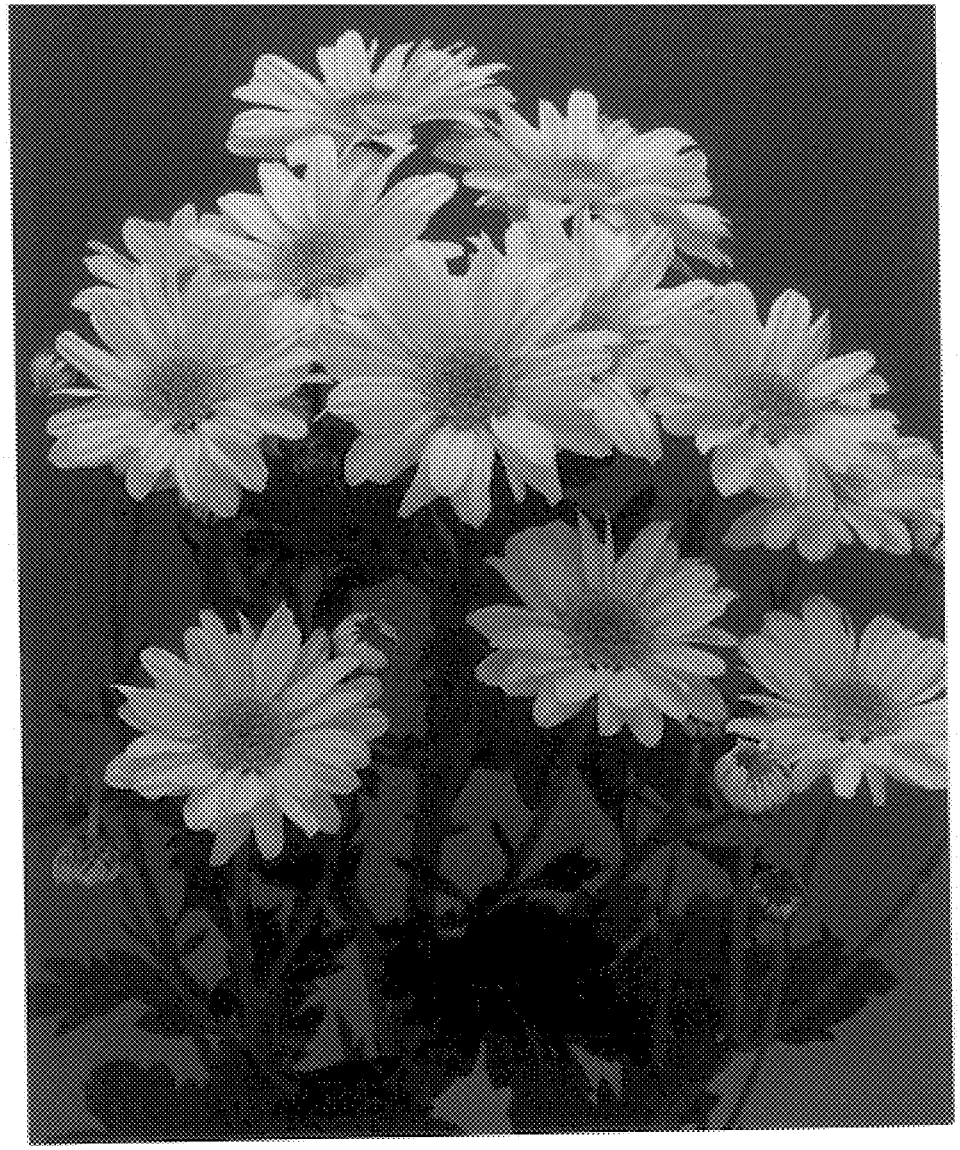

* * * * *